(12) United States Patent
Anderson (10) Patent No.: US 7,015,859 B2
(45) Date of Patent: Mar. 21, 2006

(54) ELECTROMAGNETIC TRACKING SYSTEM AND METHOD USING A THREE-COIL WIRELESS TRANSMITTER

(75) Inventor: Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/869,396

(22) Filed: Jun. 16, 2004

(65) Prior Publication Data

US 2005/0104776 A1 May 19, 2005

Related U.S. Application Data (60) Provisional application No. 60/520,189, filed on Nov. 14, 2003.

(51) Int. Cl.
 *G01S 3/02* (2006.01)
(52) U.S. Cl. .................................. 342/450; 342/463
(58) Field of Classification Search ........... 342/357.07, 342/450, 457, 463; 455/456.1, 457
See application file for complete search history.

(56) References Cited

U.S. PATENT DOCUMENTS

| | | | |
|---|---|---|---|
| 3,392,390 A * | 7/1968 | Friedrich ..................... 342/465 |
| 3,828,867 A * | 8/1974 | Elwood ......................... 175/45 |
| 3,868,565 A | 2/1975 | Kuipers |
| 3,983,474 A | 9/1976 | Kuipers |
| 4,054,881 A | 10/1977 | Raab |
| 4,176,662 A | 12/1979 | Frazier |
| 4,613,866 A | 9/1986 | Blood |
| 4,618,822 A | 10/1986 | Hansen |
| 4,622,644 A | 11/1986 | Hansen |
| 4,642,786 A | 2/1987 | Hansen |
| 4,710,708 A | 12/1987 | Rorden et al. |
| 4,737,794 A | 4/1988 | Jones |
| 4,742,356 A | 5/1988 | Kuipers |
| 4,820,041 A * | 4/1989 | Davidson et al. .......... 356/3.12 |
| 5,099,845 A | 3/1992 | Besz et al. |
| 5,107,746 A * | 4/1992 | Bauer .......................... 84/626 |
| 5,211,165 A | 5/1993 | Dumoulin et al. |
| 5,251,635 A | 10/1993 | Dumoulin et al. |
| 5,255,680 A | 10/1993 | Darrow |
| 5,265,610 A | 11/1993 | Darrow |
| 5,307,072 A | 4/1994 | Jones |

(Continued)

FOREIGN PATENT DOCUMENTS

EP 0 531 081 A1 3/1993

(Continued)

OTHER PUBLICATIONS

Peter T. Anderson, A Source of Accurately Calculable Quasi-Static Magnetic Fields, Oct. 2001.

(Continued)

*Primary Examiner*—Dao Phan
(74) *Attorney, Agent, or Firm*—McAndrews, Held & Malloy, Ltd.; Peter J. Vogel; Michael A. Dellapenna (57) ABSTRACT

Certain embodiments of the present invention provide a system and method for electromagnetic tracking using a three-coil wireless transmitter. The electromagnetic tracking system includes an instrument manipulated by a user to perform a task, a wireless transmitter for broadcasting a wireless signal, a receiver assembly for receiving the wireless signal, and electronics for determining positioning information for the instrument based on a relationship between the receiver assembly and the wireless transmitter. In an embodiment, the wireless transmitter includes a wireless transmitter coil trio. In an embodiment, the receiver assembly includes two receiver coil trios.

26 Claims, 6 Drawing Sheets

U.S. PATENT DOCUMENTS

| | | | |
|---|---|---|---|
| 5,377,678 A | 1/1995 | Dumoulin et al. | |
| 5,425,367 A | 6/1995 | Shapiro | |
| 5,425,382 A | 6/1995 | Golden et al. | |
| 5,437,277 A | 8/1995 | Dumoulin | |
| 5,443,066 A | 8/1995 | Dumoulin et al. | |
| 5,445,150 A | 8/1995 | Dumoulin et al. | |
| 5,517,195 A | 5/1996 | Narlow et al. | |
| 5,558,091 A | 9/1996 | Acker | |
| 5,592,939 A | 1/1997 | Martinelli | |
| 5,622,169 A | 4/1997 | Golden et al. | |
| 5,715,042 A * | 2/1998 | Milani et al. | 356/3.12 |
| 6,052,610 A | 4/2000 | Koch | |
| 6,073,043 A | 6/2000 | Schneider | |
| 6,129,667 A | 10/2000 | Dumoulin | |
| 6,129,668 A | 10/2000 | Haynor et al. | |
| 6,177,792 B1 | 1/2001 | Govari | |
| 6,188,355 B1 | 2/2001 | Gilboa | |
| 6,201,987 B1 | 3/2001 | Dumoulin | |
| 6,226,547 B1 | 5/2001 | Lockhart | |
| 6,230,038 B1 | 5/2001 | von Gutfeld et al. | |
| 6,233,476 B1 | 5/2001 | Strommer et al. | |
| 6,259,372 B1 | 7/2001 | Taranowski et al. | |
| 6,341,231 B1 * | 1/2002 | Ferre et al. | 600/424 |
| 6,369,564 B1 | 4/2002 | Khalfin et al. | |
| 6,374,131 B1 | 4/2002 | Tomita et al. | |
| 6,374,134 B1 | 4/2002 | Bladen | |
| 6,427,079 B1 | 7/2002 | Schneider et al. | |
| 6,459,882 B1 | 10/2002 | Palermo | |
| 6,463,039 B1 | 10/2002 | Ricci | |
| 6,472,975 B1 | 10/2002 | Beigel et al. | |

FOREIGN PATENT DOCUMENTS

| | | |
|---|---|---|
| EP | 1 493 384 A1 | 1/2005 |

OTHER PUBLICATIONS

Tom Ahlkvist Scharfeld, An Analysis of the Fundamental Constraints on Low Cost Passive Radio-Frequency Identification System Design, Aug. 2001.

* cited by examiner

ELECTROMAGNETIC TRACKING SYSTEM AND METHOD USING A THREE-COIL WIRELESS TRANSMITTER

RELATED APPLICATIONS

The present application relates to, and claims priority from, U.S. Provisional Application No. 60/520,189 filed on Nov. 14, 2003, and entitled "Electromagnetic Tracking System and Method Using a Three-Coil Wireless Transmitter".

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to an electromagnetic tracking system. In particular, the present invention relates to an electromagnetic tracking system using a wireless transmitter.

Many medical procedures involve a medical instrument, such as a drill, a catheter, scalpel, scope, stent or other tool. In some cases, a medical imaging or video system may be used to provide positioning information for the instrument, as well as visualization of an interior of a patient. However, medical practitioners often do not have the use of medical imaging systems when performing medical procedures. Typically, medical imaging systems are too slow to produce useable real-time images for instrument tracking in medical procedures. The use of medical imaging systems for instrument tracking may be also limited for health and safety reasons (e.g., radiation dosage concerns), financial limitations, physical space restrictions, and other concerns, for example.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may also be used to track the position of items other than medical instruments in a variety of applications. That is, a tracking system may be used in other settings where the position of an instrument in an object or an environment is unable to be accurately determined by visual inspection. For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Tracking systems used to track larger objects, such as airplanes in relation to an airport, involve less accurate measurements than system that track smaller objects, such as surgical instruments. Additionally, it is desirable to use small, low power, and low cost tracking devices to track small objects, such as medical instruments. Thus, a tracking system providing accurate measurements using small, low cost and low power components would be highly desirable.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

Figure 6:
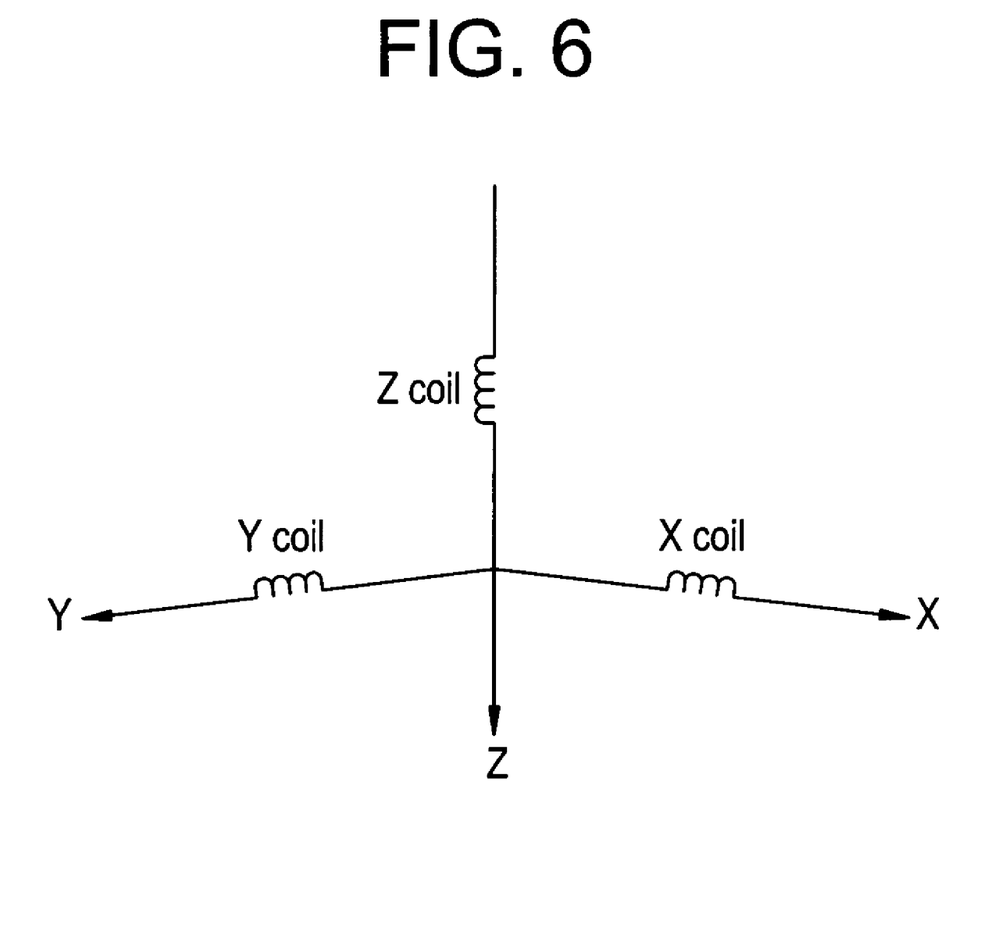
FIG. 6 illustrates a dipole coil trio used in accordance with an embodiment of the present invention.

The ISCA tracker architecture uses a three-axis dipole coil transmitter and a three-axis dipole coil receiver. Each three-axis transmitter or receiver is built so that the three coils exhibit approximately the same effective area, are oriented approximately orthogonally to one another, and are centered at approximately the same point. An example of a dipole coil trio with coils in X, Y, and Z directions spaced approximately equally about a center point is shown in FIG. 6. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. Using nine mutual inductance measurements, for example, a three degrees of freedom position and a three degrees of freedom orientation may be obtained for the transmitter. Thus, a method for improved determination of position and orientation would be highly desirable.

Some existing electromagnetic tracking systems include a transmitter and receiver wired to a common device or box. In system with the transmitter and receiver wired to a common device, the object being tracked is wired to the same device as the components performing the tracking. Thus, the range of motion of the object being tracked is limited.

Thus, a need exists for a tracking system that allows improved tracking of an instrument. Additionally, a need exists for an electromagnetic tracking system allowing increased mobility and flexibility. A need also exists for electromagnetic surgical navigation system that allows surgical or other medical procedures to be performed in a less invasive manner.

BRIEF SUMMARY OF THE INVENTION

Certain embodiments of the present invention provide a system and method for electromagnetic tracking using a three-coil wireless transmitter. The electromagnetic tracking system includes an instrument manipulated by a user to perform a task, a wireless transmitter for broadcasting a wireless signal, a receiver assembly for receiving the wireless signal, and electronics for determining positioning information for the instrument based on a relationship between the receiver assembly and the wireless transmitter. The wireless transmitter is located on the instrument. In an embodiment, the wireless transmitter includes a wireless transmitter coil trio. In an embodiment, the receiver assembly includes two receiver coil trios.

In an embodiment, the instrument is a medical instrument. In an embodiment, the instrument may be used to perform a task that involves manipulating the instrument outside of the user's line of sight. The system may also include a wired transmitter located away from the instrument. The wired transmitter may be located on an instrument guide for the instrument, for example. The receiver assembly may also be located on the instrument guide.

In an embodiment, the relationship between the receiver assembly and the wireless transmitter includes triangulation between the wireless transmitter and the receiver assembly. The positioning information may include position and/or orientation information for the instrument. The positioning information may be determined by a range and a gain ratio between the wireless transmitter and the receiver assembly. The positioning information may also be determined using mutual inductance between the wireless transmitter and the receiver assembly.

Certain embodiments include a method for tracking a position of an instrument. The method includes transmitting a signal from a wireless transmitter located on an instrument, receiving the signal at a receiver assembly, and determining positioning information for the wireless transmitter based on the signal and a relationship between the wireless transmitter and the receiver assembly.

The method may also include transmitting a signal from a second transmitter to determine the position information. Additionally, the method may include determining a magnitude and phase of the signal. The method may also include calculating a sum of products of the signal. In an embodiment, the method may include determining a mutual inductance between the wireless transmitter and the receiver assembly. The method may also include refining the positioning information using a solution fitter. The method may also include displaying said positioning information with respect to a reference system.

In an embodiment, the determining step further includes determining positioning information for the wireless transmitter by triangulating between the wireless transmitter and the receiver assembly. The determining step may also include determining positioning information for the wireless transmitter by determining a range and a gain ratio between the wireless transmitter and the receiver assembly.

Certain embodiments include an improved wireless electromagnetic tracking system. The tracking system includes a wireless transmitter coil trio attached to an object and transmitting a signal. The system also includes a receiver assembly with at least two receiver coil trios. The system further includes a tracker electronics for determining positioning information for the wireless coil based on the wireless coil and the two or more receiver coil trios. The system may also include a display for displaying the positioning information. In an embodiment, the positioning information may be determined based on the signal and a triangulation of signals between the wireless coil trio and the two or more receiver coil trios. The positioning information may also be determined based on a mutual inductance between the wireless coil trio and the two or more receiver coil trios.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiment of an electromagnetic tracking system used with an image-guided surgery system. It is understood that the present invention may be used with other imaging systems and other applications.

Figure 1:
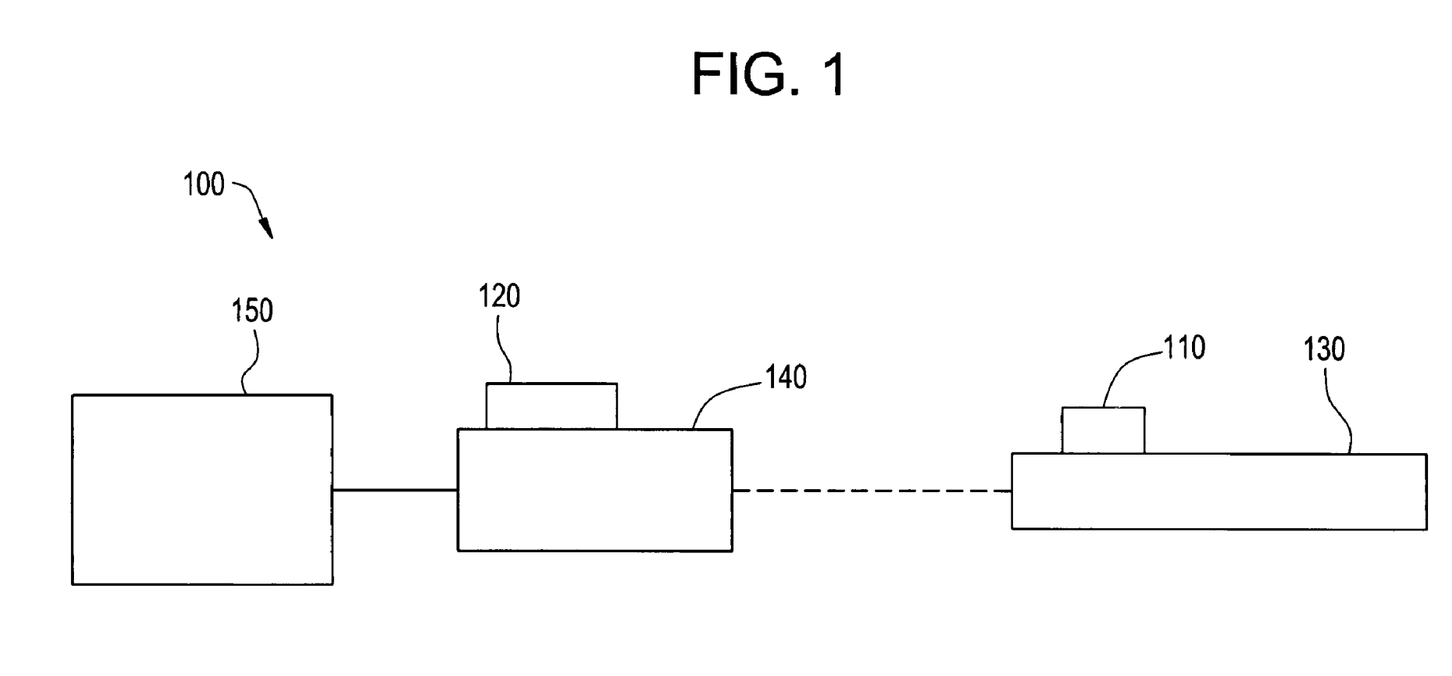
FIG. 1 illustrates an electromagnetic tracking system used in accordance with an embodiment of the present invention.

FIG. 1 illustrates an electromagnetic tracking system 100 used in accordance with an embodiment of the present invention. The tracking system 100 includes a wireless transmitter 110, a receiver assembly 120, an instrument 130, an instrument guide 140, and a tracker electronics 150. In an embodiment, the wireless transmitter 110 is positioned on the instrument 130. The receiver assembly 120 is located remotely from the instrument 130 and the transmitter 110. The instrument guide 140 is used to control the instrument 130.

In an embodiment, the tracker electronics 150 includes a Lucas 4650 processor. The tracker electronics 150 may be integrated with the receiver assembly 120 or may be a separate module, for example. In an embodiment, the tracker electronics 150 resides on a receiver assembly 120 board to perform a Sum of Products (SOP) and other calculations on signal data. In an embodiment, a SOP calculation is a component of a windowed discrete Fourier transform. An SOP may be calculated using the following equation:

$$y = \sum_{n=1}^{k} a_n * x_n, \text{ or } SOP_n = \sum_{M=n-1}^{1} W_M A_k, \quad (1)$$

wherein $W_M$ defines a weight function and $A_k$ is a tracker data sample from an analog-to-digital converter (ADC). For example, if an output is sampled every 2880 ADC samples, $$SOP = \sum_{M=2879}^{1} W_M A_{2880(n-1)+M}.$$

In an embodiment, the receiver assembly 120 includes two receivers 122, 124. The receivers 122, 124 of the receiver assembly 120 may be receiver dipole coils or coil trios, for example. The receiver assembly 120 may be attached to the instrument guide 140. The instrument 130 may be a surgical drill or other medical instrument, for example. The instrument guide 140 may be a drill guide or other medical instrument guide, for example. In another embodiment, the instrument 130 with instrument guide 140 may be a tool that is indirectly controlled for applications wherein an operator's field of vision is obscured by an object.

In certain embodiments, the wireless transmitter 110 is attached to the instrument 130. Alternatively, the wireless transmitter 110 may be integrated with the instrument 130. Using the wireless transmitter 110 and receiver assembly 120, the position of the instrument 130 is tracked with respect to the instrument guide 140 or other reference point, for example.

The system 100 may also include one or more additional transmitters (not shown) for use in instrument 130 tracking. The additional transmitter(s) may be wired or wireless transmitter(s). For example, a wireless second transmitter may be located on the instrument guide 140 or on the instrument 130. Alternatively, for example, a wired second transmitter may be located on the instrument guide 140. The second transmitter may be wired to the tracker electronics 150. A cable may be run from the instrument 130 to the tracker electronics 150. The wireless transmitter 110 and additional transmitter(s) may be tracked simultaneously from the receivers in the receiver assembly 120.

In an embodiment, the wireless transmitter 110 may be a wireless ISCA transmitter, such as a wireless ISCA transmitter coil trio, for example. The wireless transmitter 110 eliminates the need for a cable connecting the instrument 130 to the tracker electronics 150. Software running with the tracker electronics 150 may be reconfigured to accommodate the wireless transmitter 110 rather than, or in addition to, a wired transmitter. The wireless transmitter 110 may draw power from the instrument 130 or may have a separate power source, such as a battery or photocell, for example. The wireless transmitter 110 may receive energy from one magnetic field (a drive field) and transmit energy in another magnetic field (a response field). The wireless transmitter 110 may be tracked from each of the receivers in the receiver assembly 120. Thus, certain embodiments use a wireless transmitter 110 and a wired receiver assembly 120 to track the position of the instrument 130 with respect to the instrument guide 140.

In an embodiment, a gain ratio of the signal received from the transmitter 110 is known but an absolute gain in the receiver assembly 120 may not be known. The tracker electronics 150 may determine the wireless transmitter 110 position with respect to the instrument guide 140 or other reference point. The direction or orientation of the transmitter 110 position may be determined from the received signals and gain ratio. However, a tracked position of the transmitter 110 may have range errors (i.e., the tracked position is in the right direction but not at the right distance). To determine a correct range, the tracker electronics 150 may triangulate on the tracked positions of the transmitter 110 from the receivers and use the positional relationship between the two receivers 122, 124 in the receiver array 120.

As an example, the instrument 130 may be a surgical drill. The instrument guide 140 is a drill guide for the drill. The wireless transmitter 110 includes a coil trio and transmission electronics is located on the drill. The receiver assembly 120 is located on the drill guide. The receiver assembly 120 includes two receiver 122, 124 coil trios.

In operation, the drill is used to operate inside a patient and is controlled by the drill guide. The wireless transmitter 110 mounted on the drill draws power from a power source in the drill and transmits a signal at a given frequency. The receivers 122, 124 in the receiver assembly 120 detect the signal transmitted by the wireless transmitter 110 coil.

Mutual inductance may be used in the electromagnetic tracking system to identify the positions of components in the system. Mutual inductance may allow the system to be divided into two parts: coils and electronics. Determining mutual inductance involves a physical design of the coils and a geometrical relationship between the coils but not details of the electronics used to measure the mutual inductance. Additionally, mutual inductance does not depend on which coil receives an applied current.

In addition to the electronics used to measure mutual inductance, a system including one transmitter coil and one receiver coil forms a four-terminal two-port network. A varying current injected into one coil induces a voltage in the other coil. The induced voltage V is proportional to the rate of change of the applied current I:

$$V = L_m (dI/dt) \quad (2),$$

wherein $L_m$ represents mutual inductance. $L_m$ is based on the geometry of the coils (closed circuits). $L_m$ is a ratio independent of applied current waveform or frequency. Thus, $L_m$ is a well-defined property that may be measured with reasonable precision. Some additional information regarding mutual inductance, SOP calculations and tracking may be found in "PhD Thesis", Peter T. Anderson, U, Date, herein incorporated by reference.

In an embodiment, a positional relationship between the receiver 122, 124 coils in the receiver assembly 120 is known. The receiver 122, 124 coils receive the signal transmitted by the wireless transmitter 110 coil. The position and orientation of the wireless transmitter 110 relative to a reference coordinate system may then be determined using the mutual inductance between the receiver 122, 124 and transmitter 110 coils and the positional relationship between the receiver 122, 124 coils. The resulting tracked position and orientation of the wireless transmitter 110 attached to the drill in relation to the receiver assembly 120 on the drill guide may be used to help a user manipulate the drill inside the patient's body. Positioning information may help prevent injury to the patient and minimize unnecessary risk.

In certain embodiments, the electromagnetic tracking system 100 allows for the object being tracked to move freely without being limited by connections with a transmitter 110 or receiver 122, 124. To reduce the bulk associated with attaching a battery or other power source to a transponder, passive transponders may employ a coil as a means of coupling with and receiving power from other devices.

In certain embodiments, ratios between fields are measured, rather than absolute values. Precise ratios may be easier to obtain than precise absolute values. Five of six degrees of freedom for position and orientation measurements may be determined from ratios of received magnetic fields or mutual inductances, for example. Range (e.g., a distance from a receiver to a transmitter) may not be determined without a field strength or mutual inductance value.

In an embodiment, two receiver 122, 124 coil trios, such as ISCA receiver coil trios, are used to determine range. Position and orientation parameters, aside from range, may be determined using magnetic field or mutual inductance ratio measurements from the six receivers in the two receiver 122, 124 coil trios. Additionally, a ratio of the ranges between the two receiver 122, 124 coil trios and the transmitter 110 coil trio may be determined. Thus, a triangle is formed between the transmitter 110 and receiver 122, 124 coil trios. The three angles of the triangle may be determined by ratio measurements. Additionally, a ratio of the two ranges is also determined. Using the three angles and the ratio of the two sides, the ratios of all three sides of the triangle may be determined. The side of the triangle that represents a distance between the two receiver 122, 124 coil trios may be determined based on construction of the receiver assembly 120. Thus, by triangulation, the ranges between the two receivers 122, 124 and the transmitter 110 may be determined (i.e., the remaining two sides of the triangle).

Figure 2:
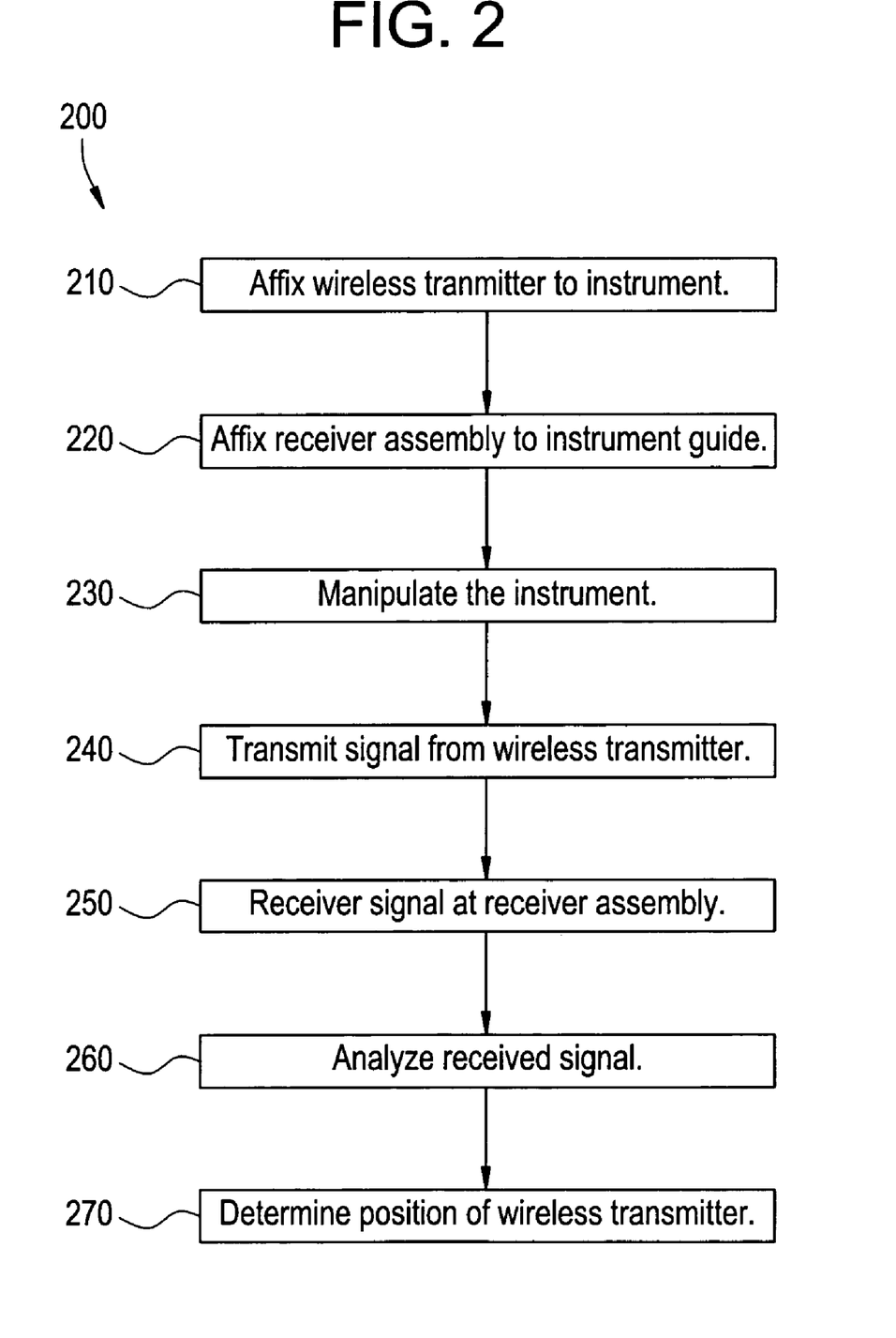
FIG. 2 illustrates a flow diagram for a method for tracking a position of an instrument used in accordance with an embodiment of the present invention.

FIG. 2 illustrates a flow diagram for a method 200 for tracking a position of an instrument 130 used in accordance with an embodiment of the present invention. First, at step 210, the wireless transmitter 110 is affixed to an instrument 130, such as a surgical drill or other medical instrument or tool. Next, at step 220, the receiver assembly 120 is affixed to the instrument guide 140. In an embodiment, the wireless transmitter 110 includes a transmitter coil trio. In an embodiment, the receiver assembly 120 includes two receiver 122, 124 coil trios.

Then, at step 230, an operator manipulates the instrument 130 inside the patient using the instrument guide 140. At step 240, the wireless transmitter 110 broadcasts a signal using power from the instrument 140. For example, the electronics of the wireless transmitter 110 generate a signal using the coil of the wireless transmitter 110.

Next, at step 250, the receivers of the receiver assembly 120 detect the signal transmitted from the wireless transmitter 110. At step 260, the received signals are analyzed.

The tracker electronics 150 measure the signals as received by the receivers 122, 124. The signals are measured based on the relationship between the receivers 122, 124 in the receiver assembly 120.

Figure 3:
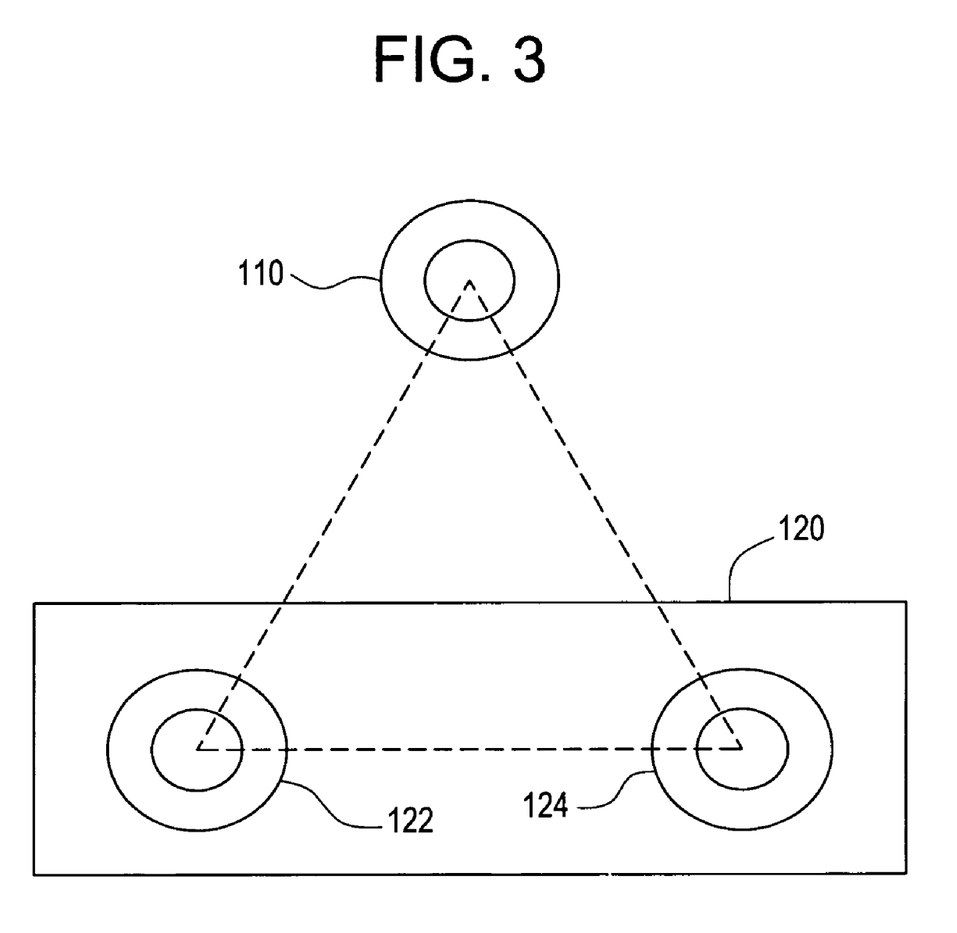
FIG. 3 illustrates triangulation between a wireless transmitter and two receivers in a receiver assembly used in accordance with an embodiment of the present invention.

Then, at step 270, the position of the transmitter 110 is determined. The wireless transmitter 110 position may be determined with respect to the instrument guide 140 or other reference coordinate system. The direction or orientation of the transmitter 110 position may be determined from the received signals. As illustrated in FIG. 3, triangulation may determine a range to the transmitter 110 based on the tracked positions of the transmitter 110 from the receivers and on the positional relationship between the two receivers 122, 124 in the receiver array 120. In an alternative embodiment, a wired transmitter also transmits a signal to the receiver assembly 120 to help locate the instrument 130. Further illustrations of a wireless electromagnetic tracking system and method used in accordance with certain embodiments of the present invention are provided below.

Figure 4:
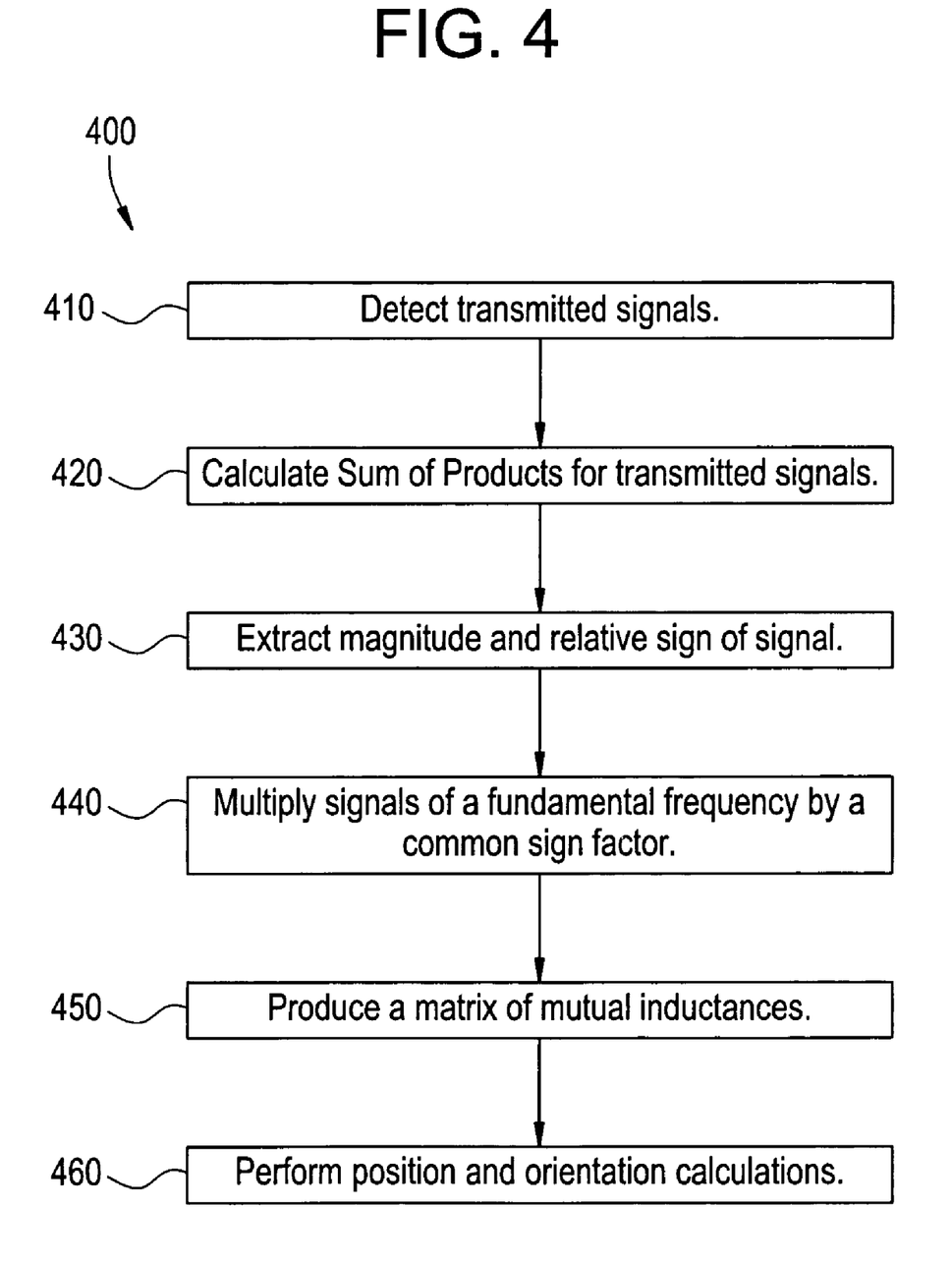
FIG. 4 shows a flow diagram for a method for determining a magnitude and relative sign or phase of each signal received by a receiver from the wireless transmitter used in accordance with an embodiment of the present invention.

FIG. 4 shows a flow diagram for a method 400 for determining a magnitude and relative sign or phase of each signal received by a receiver 122, 124 from the wireless transmitter 110 used in accordance with an embodiment of the present invention. At step 410, signals transmitted by the wireless transmitted signals are detected by the receiver coils. Then at step 420, one or more Sums of Products (SOPs) are calculated for the wireless transmitted signals.

The tracker electronics 150 may determine SOPs for the signals received by the receiver 122, 124 coils in the receiver assembly 120. SOPs may be calculated from each of the received signals to determine a signal phase. In an embodiment, signals transmitted by the wireless transmitter 110 are received by the receiver 122, 124 coils. The receiver 122, 124 coils may receive signals transmitted by another transmitter as well. Each coil driver outputs a sinusoidal voltage at a unique frequency. Each output frequency is different from the frequencies output by other drivers. SOP calculations extract frequency components from the receiver coil voltages.

The SOPs may be used by software, for example, to determine a phase of the received signals. The phase of the signal may be determined by phase-locking or another phase-determining calculation, for example. Since a signal may be positive or negative, the phase may be locked at 0 degrees or at 180 degrees, for example. However, since a phase lock may occur at 0 or 180 degrees, two successive locks on the same signal may occur at different phases. Therefore, the sign of the signal may be distinguished from the sign of the lock.

In an embodiment, the wireless transmitter 110 coil emits a first signal at a fundamental frequency and a second signal at a second harmonic frequency. The second harmonic frequency is emitted at a low amplitude and is phased so that the sign of the fundamental frequency may be determined separately from the sign of the lock. In an embodiment, a second harmonic frequency may be used to determine phase, using such methods as phase-disambiguation (also known as polarity determination). The second harmonic may be used to determine polarity (or phase 0 degrees versus 180 degrees) of a transmitter signal.

In an alternative embodiment, an SOP is generated at the fundamental frequency for six receiver coils in order to obtain position tracking data. An SOP of the second harmonic is obtained for three of the six receiver coils (one trio) because all of the signals may be forced to lock the same way. In an embodiment, a measure of current is not SOPed at the wireless frequencies because current at the wireless transmitter 110 may not be known.

At step 430, once the wireless transmitter 110 signals have been reduced to SOPs, a magnitude and relative sign of each wireless transmitter 110 signal may be extracted. In an embodiment, a tip of the transmitter 110 is assumed to be pointing towards the receiver assembly 120. Additionally, the mutual inductance between the transmitter 110 coil and receiver 122, 124 coil may be assumed to be large. The phase of the transmitter 110 current may then be calculated from the receiver 122, 124 coil signal.

To determine a magnitude of the received signals, a gain of a receiver coil channel is determined. In an embodiment, receiver 122, 124 gain may be measured and stored prior to tracking. The stored receiver gain may be used during tracking of the instrument 130. Gain may be measured using a receiver assembly 120 calculator. SOP matrices of the received signals may be used to calculate gain. Successive SOP measurements are averaged to produce an averaged SOP matrix. A complex scalar calibration voltage and complex vector calibration voltage may be extracted. A current-to-voltage transimpedance of a channel measuring current is also calculated. Calibration drive current, coil frequency, and mutual impedance are also determined. An inverse gain vector may then be calculated using the calibration mutual impedance, drive current, and complex voltage vector. For example, an inverse gain vector may be represented as follows:

$$\text{inverse\_gain}[n] = \text{mutual\_impedance} \times (\text{drive\_current}/\text{voltage}[n]) \quad (3).$$

For an ideal receiver assembly 120, the inverse gains are 1+j0 (e.g., no imaginary component).

A transmitter 110 driver current may be calculated based on SOPs for the appropriate transmitter frequency index and the current-to-voltage transimpedance of the current-measuring channel. The transmitter current is a product of current magnitude and current phase. In an embodiment, the magnitude is real, positive, and constant. The phase is complex and of unity magnitude.

Then, a matrix of SOP values for the received signal and the inverse gain vector may be used to calculate a normalized receiver signal vector. Next, a complex mutual inductance vector may be determined from the receiver signal, transmitter driver current, and transmitter frequency. In an embodiment, the mutual inductance vector is a complex quantity with an imaginary component. However, if the vector phase is correct, the imaginary component is approximately zero. A solution fitter, such as a Powell solution filter, may then be used to determine optimum values of transmitter 110 position, orientation, and gain. The solution fitter is seeded with the transmitter 110 position, orientation, and gain from a previous cycle.

In an embodiment, a denormalized transmitter current phase may be calculated using the largest-magnitude received signal and a sign of +1 or −1 to produce received signal elements with consistent signs over time. Selecting a sign is described further below. Then, the phase of the transmitter 110 current may be corrected using the denormalized transmitter current phase and sign. The transmitter 110 complex current may be determined from the current magnitude and current phase. The transmitter 110 current may then be used to calculate the mutual inductance vector.

Then, at step 440, all of the signals of a given fundamental frequency may be multiplied by a common sign factor of +1 or −1, for example, to correct the signs of the signals. The second harmonic signals may be used to determine whether to multiply the fundamental frequency signals by +1 or −1. Sign determination may be executed for each of the wireless transmitter 110 coils. A transmitter 110 coil is driven with a fundamental frequency sine wave current and a second harmonic frequency sine wave current. The fundamental and second harmonic frequency waves are used so that a locked sign of an induced voltage in a receiver may be the same as the sign of a voltage induced in a self-inductive reactance of the transmitter 110.

Figure 5:
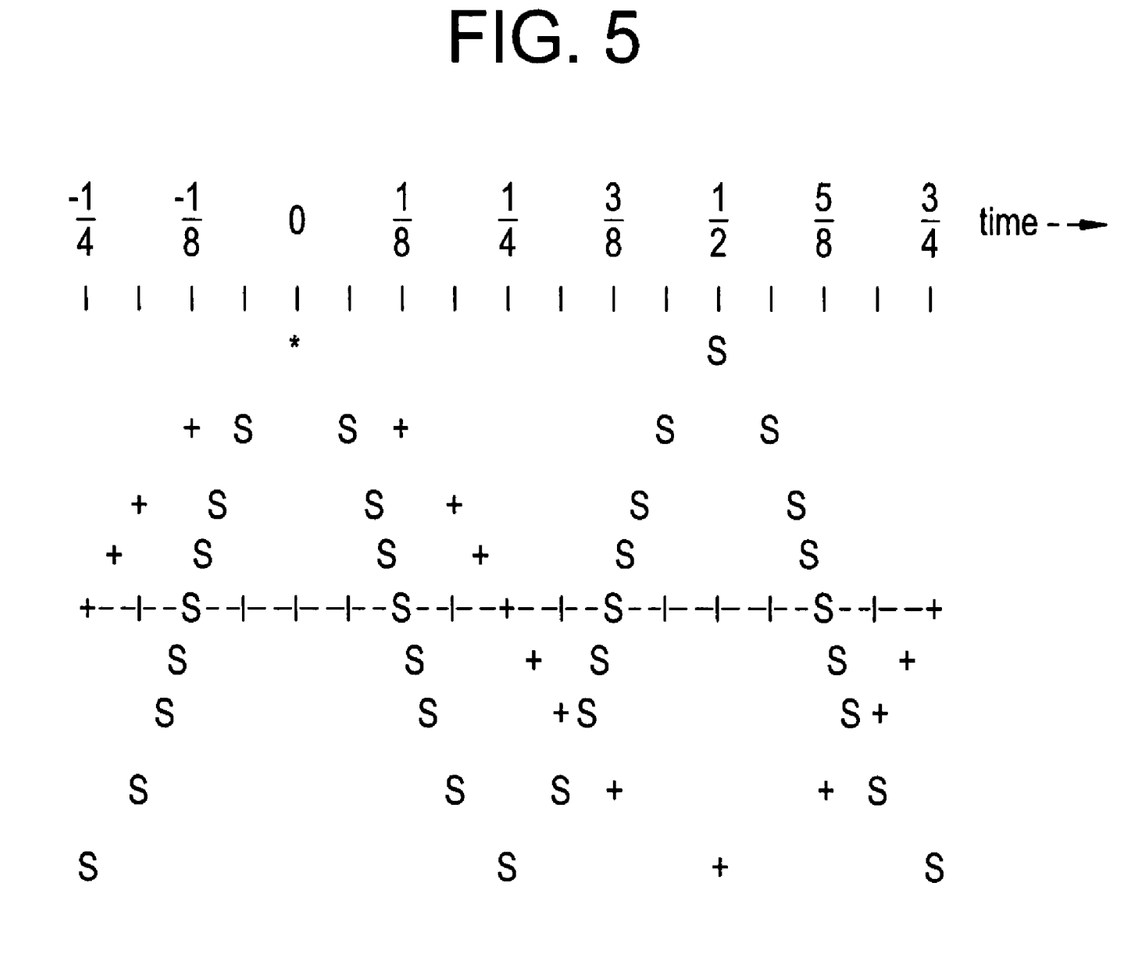
FIG. 5 illustrates a fundamental cosine wave induced voltage and a second harmonic cosine wave induced voltage with respect to time in accordance with an embodiment of the present invention.

FIG. 5 illustrates a fundamental cosine wave induced voltage and a second harmonic cosine wave induced voltage with respect to time in accordance with an embodiment of the present invention. The time is given in fractions of a fundamental cosine wave cycle. In an embodiment, a group delay is more than a one cycle of a fundamental frequency. However, fractional cycle delays at the fundamental frequency may be considered because a cycle of fundamental frequency delay equals two cycles of a second harmonic delay. The phase of the fundamental frequency may be locked or recovered by determining a time of a positive peak of the fundamental frequency received signal. A second harmonic frequency may be used to determine the sign of the received signal.

A "+" curve shown in FIG. 5 represents one cycle of a fundamental cosine wave induced voltage of the receiver 122, 124. An "s" curve of FIG. 5 represents two cycles of a second harmonic cosine wave induced voltage at the receiver 122, 124. An "*" in FIG. 5 indicates a point common to both fundamental and second harmonic waves.

FIG. 5 shows that the second harmonic of the transmitted signal has positive peaks at both positive and negative peaks of the fundamental frequency. In an embodiment, a positive received signal has the same plot as the transmitted signal shown in FIG. 5. A negative received signal has both fundamental and second harmonic frequencies negated. A 180-degree phase shift in a received signal (by a wrong phase lock, for example) has a negated fundamental frequency, but the second harmonic frequency is not negated. Thus, in an embodiment, a negative received signal differs from a 180-degree phase shifted received signal by the sign of the second harmonic.

In an embodiment, a receiver 122 coil trio includes coils X1, Y1, and Z1. SOPs are calculated for I (cosine) and Q (sine) components of the fundamental frequency and I and Q components of the second harmonic frequency for coils X1, Y1, and Z1. For a second receiver 124 coil with coils X2, Y2, and Z2, SOPs may be determined for the fundamental frequency I and Q components. A receiver coil in the first coil trio having the largest magnitude signal may then be selected (receiver coil W). A fundamental frequency complex SOP of coil W (CSOPWF) is then generated, as shown below in Equation (4):

$$CSOPWF = SOP[\text{fundamental frequency } I \text{ phase}][\text{coil } W] + jSOP[\text{fundamental frequency } Q \text{ phase}][\text{coil } W] \quad (4).$$

In an embodiment, the phase of CSOPWF is of unit magnitude:

$$\text{Phase}(CSOPWF) = CSOPWF/|CSOPWF| \quad (5).$$

An inverse of the phase of CSOPWF may be determined as:

$$\text{Phaseinv}(CSOPWF) = 1/\text{phase}(CSOPWF) = |CSOPWF|/CSOPWF \quad (6).$$

Thus, multiplying CSOPWF by the inverse phase of CSOPWF produces an absolute value of CSOPWF:

$$CSOPWF*\text{phaseinv}(CSOPWF)$$
$$=CSOPWF*|CSOPWF|/CSOPWF=|CSOPWF| \quad (7).$$

In an embodiment, an absolute value fundamental frequency complex SOP of coil W is a real value, has the same magnitude as CSOPWF, and is positive. Therefore, multiplying a signal by the inverse phase of the CSOPWF rotates the vector so that the positive peak of the fundamental frequency received signal occurs at 0 degrees.

A second harmonic frequency complex SOP of coil W may be generated using equation (8):

$$CSOPW2=SOP[\text{second harmonic frequency } I \text{ phase}]$$
$$[\text{coil } W]+j \, SOP[\text{second harmonic frequency } Q \text{ phase}][\text{coil } W] \quad (8).$$

Multiplying CSOPW2 by the square of the phase inverse of CSOPWF rotates the second harmonic vector. The rotated second harmonic vector positions a part of the second harmonic frequency, which is simultaneous with the positive peak of the fundamental frequency shown in FIG. 5, at 0 degrees. A part of the second harmonic that coincides with the positive peak of the received fundamental may be a positive or negative peak of the second harmonic received signal, depending upon whether the received signal is positive or negative. Therefore, a phase factor may be calculated as follows:

$$\text{Phase\_factor}=\text{phaseinv}(CSOPWF)*\text{sign}(\text{real} \, (CSOPW2*(\text{phaseinv}(CSOPWF))^2) \quad (9).$$

Thus, a real portion of a signal from a receiver coil V (where V is X1, Y1, Z1, X2, Y2, or Z2, for example) may be determined as follows from Equations (10, 11, and 12):

$$CSOP[V]=SOP[\text{fundamental frequency } I \text{ phase}][\text{coil } V]+j \, SOP[\text{fundamental frequency } Q \text{ phase }][\text{coil } V] \quad (10).$$

A sign and phase corrected SOP of coil V may be represented as:

$$CTRSOP[V]=\text{phase\_factor}*CSOP[V] \quad (11).$$

A real SOP of coil V may be generated from Equation (12) as follows:

$$RSOP[V]=\text{real}(CTRSOP[V]) \quad (12).$$

The above equations form a phasor vector, or a vector including a complex number and normalized phase representation of a signal. In an embodiment, a phasor vector of the second harmonic rotates at twice the speed of a fundamental frequency phasor vector. The phasors are at 0 degrees (maximum positive amplitude of the cosine wave) at the same time. The second harmonic phasor is also at 0 degrees when the fundamental frequency phasor is at 180 degrees. The phasors may be shifted in time by a group delay from the receiver assembly electronics. Thus, the second harmonic frequency phasor is shifted twice as much in phase as is the fundamental frequency phasor.

The above calculations assume that the received fundamental signal is positive and determine a fractional cycle phase shift of the received fundamental signal. If the received fundamental signal is negative, then the calculated phase shift is off by 180 degrees. In an embodiment, subtracting the phase shift from the fundamental frequency phasor shifts the observed received fundamental frequency phasor to 0 degrees, regardless of the sign of the received signal. The phase shift may be subtracted from the fundamental frequency phasor by dividing the fundamental frequency phasor by the complex phase factor from Equation (8), for example. Additionally, subtracting the phase shift from the fundamental frequency phasor shifts the corrected-sign received fundamental frequency phasor to 0 degrees (for positive sign) or 180 degrees (for negative sign). Subtracting twice the phase shift (by dividing by the square of the complex phase factor, for example) shifts the sign-corrected second harmonic phasor to 0 degrees. For a negative sign, the phasor is shifted to 360 degrees, which is the same as 0 degrees. Thus, the phase-corrected second harmonic phasor has a correct sign for a determination of position and orientation. The sign of the second harmonic phasor may be used to determine the sign of the fundamental frequency received signal.

Next, at step 450, extracting the magnitude and sign of the SOPed transmitter signals produces a matrix of mutual inductances for the receiver coils. In an embodiment, two 3×3 mutual inductance matrices are produced, one for each of the two coil trios in the receiver assembly.

In one embodiment, one or more precision wireless transmitter 110 drivers are used to drive an ISCA wireless transmitter 110 so that the system exhibits three orthogonal dipole magnetic moments of equal magnitudes and nominal signs. Thus, characteristics of the dipole coils, such as the wireless transmitter 110 coil and receiver 122, 124 coils, may be determined except for a global gain. Therefore, position and orientation (P&O) solutions may include a range error but otherwise be accurate. That is, in an embodiment, performing an ISCA P&O calculation for each receiver coil trio produces P&O results that are accurate except for a common range scale factor error. Adding a precision reference allows control of global gain. However, the gain of the receiver assembly 120 and/or tracker electronics 150 may not be precisely known.

In an embodiment, two receiver 122, 124 coil trios in the receiver assembly 120 and the wireless transmitter 110 form a triangle. Angles of the triangle may be determined. Thus, ratios of the sides of the triangle may also be determined. Additionally, spacing between the two receivers 122, 124 may be determined. The spacing between the receivers 122, 124 represents one side of the triangle. A range scale factor that corresponds to the spacing between receivers 122, 124 may be calculated. The range scale factor may be used to correct the P&O calculation. The range scale factor may be used to correct the measurement of the length between the receivers 122, 124 to generate an accurate P&O for the wireless transmitter 110.

In another embodiment, one or more non-precision wireless transmitter 110 drivers are used to drive a wireless transmitter coil trio to produce three wireless transmitter dipole moments that are approximately orthogonal and of approximately equal magnitudes. That is, the transmitter coils are preferably designed with approximately nominal gains and are approximately orthogonal. The non-precision drivers drive the transmitter coil trio with nominal waveforms to give the desired fundamentals and second harmonics for an approximately nominal transmitter coil trio.

A nominal transmitter coil is perfectly orthogonal with nominal coil gains and nominal signs for the coil trio. The nominal gains of the nominal coil trio are different, since the coils are of slightly different nominal sizes (for example, the coils nest in one another). In an embodiment, the wireless transmitter 110 and other transmitters in the system 100 are built with approximately nominal gain and approximately perfect orthogonality. However, signs of the coil gains for the transmitter coil trio may not be controlled.

In an embodiment, the signs of the coil gains may impact the P&O determination. If two signs are reversed, the coil trio will appear to be rotated 180 degrees. A rotation by 180 degrees changes an even number of signs. A mirror-image (known as a perversion in optics) operation may change one or all three signs.

A solution fitter may be applied to determine a goodness of fit of coil gain and sign. Then, the sign on one gain may be reversed. The solution fitter is rerun with the sign of one gain reversed to obtain a second goodness of fit measurement. The solution providing a better goodness of fit is selected. For some solution fitters or solvers, the fitter may not find a solution for one of the two gain cases, corresponding to an impermissible rotation. If one solution is not found, the other solution is used. As described above, an incorrect sign indicates an impermissible rotation and may cause the solution fitter to fail.

If the orientation of transmitter coils within a transmitter housing is unimportant, then the sign of transmitter coil X and the sign of transmitter coil Y in a coil trio XYZ may be viewed as correct, since a wrong sign is the same as a 180-degree rotation in the transmitter. A sign of transmitter Z coil sign may be determined during the P&O calculation. If the orientation of the transmitter coils with in the housing is important, then transmitter X and Y coils are wired correctly. Transmitter Z coil may not be wired correctly.

Then, at step 460, when the magnitude and phase of the received signals and the mutual inductance matrix have been determined, P&O calculations are performed for the transmitter coil trio. In an embodiment, approximate P&O of the wireless transmitter 110 is determined based on the inequality and nonorthogonality of the wireless transmitter moment. A solution fitter may be used to refine the P&O results. A goodness-of-fit (GOF) measurement may be determined to measure differences between measured and modeled mutual inductance, and thus P&O calculations. A global fit of eighteen mutual inductances between the six receiver coils and the three wireless transmitter coils is executed to determine P&O, transmitter dipole moment magnitudes, and transmitter dipole orthogonalities.

For example, a mutual inductance between two closed conducting circuits, a transmitter (t) and a receiver (r) may be represented by:

$$L_{mir} = \frac{U_o}{4\pi} \int_t \int_r \frac{\overline{dsr} \cdot \overline{dst}}{R_{tr}},$$

where $U_o$ is a permeability of free space, $\overline{dst}$ represents a length element of circuit t, $\overline{dsr}$ is a length element of circuit r, . is a dot product of two vectors, Rtr is a vector from $\overline{dst}$ to $\overline{dsr}$, and $R_{tr}$ is a magnitude of $R_{tr}$. Using a dipole approximation, three transmitter coils centered on a point and orthogonal to each other, and three receiver coils centered on a point and orthogonal to each other, the mutual inductance between transmitter coil t and receiver coil r may be represented by:

$$L_{m[t][r]} = \frac{K}{R^{\wedge}3}(3(\hat{t}^{\wedge} \cdot \overline{R}^{\wedge})(\overline{r}^{\wedge} \cdot \overline{R}^{\wedge}) - \hat{t}^{\wedge} \cdot \hat{r}^{\wedge}),$$

where $$K = \frac{U_o A_{efft} A_{effr}}{4\pi},$$

$\overline{R} = R[0]\hat{X}^{\wedge} + R[1]\hat{Y}^{\wedge} + R[2]\hat{Z}^{\wedge}$ = vector from transmitter coil to receiver coil, R=magnitude of $\overline{R}$, $\overline{R}^{\wedge}$=unit vector in $\overline{R}$ direction, $\hat{t}^{\wedge} = \hat{X}^{\wedge}, \hat{Y}^{\wedge}$, or $\hat{Z}^{\wedge}$ for t=0, 1, or 2 respectively, and $\hat{r}^{\wedge} = \hat{A}^{\wedge}, \hat{B}^{\wedge}$, or $\hat{C}^{\wedge}$ for r=0, 1, or 2 respectively. The receiver position may be described as $\overline{R} = (R[0], R[1], R[2])$. The receiver orientation may be described using $\hat{A}^{\wedge}, \hat{B}^{\wedge}$, and $\hat{C}^{\wedge}$. The tracking system may measure $L_{m[t][r]}$ for all nine, for example, combinations of t and r. The position, $\overline{R}$, and orientation, or equivalent, may then be calculated by mathematically inverting the above equation for $L_{m[t][r]}$. The squares of the position components R[0], R[1], R[2] may be obtained and their signs determined using squares of the mutual inductance measurements.

Thus, certain embodiments of the present invention provide a system and method for wireless tracking. The instrument and the tracking system may or may not be wired together during operation. Using a wireless transmitter eliminates the cable between the instrument and the tracking system used by a wired transmitter or receiver. Additionally, a wireless transmitter may be used with an existing tracking system. Software may be modified to operate the tracking system with the wireless transmitter, rather than changing hardware for a wired transmitter. Furthermore, the wireless transmitter eliminates use of a receiver assembly multiplexer and associated cables. In an embodiment, two ISCA receivers may be used to determine range of a transmitter coil or coils.

Certain embodiments provide a tracking system that tracks multiple transmitters from a single receiver assembly. Certain embodiments provide wireless transmitter(s) that operate on low power. Certain embodiments eliminate a transmitter data link since the wireless transmitter has no data to transmit.

Certain embodiments allow an instrument, such as a surgical instrument, to be tracked in a patient by an operator. Certain embodiments use a second harmonic frequency to determine phase, using such methods as phase-disambiguation (also known as polarity determination). The second harmonic may be used to determine polarity (or phase 0 degrees versus 180 degrees) of a transmitter signal.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An electromagnetic tracking system, said system comprising:
   an instrument manipulated by a user to perform a task;
   a wireless transmitter for broadcasting a wireless signal, said wireless transmitter located on said instrument;
   a receiver assembly for receiving said wireless signal; and
   electronics for determining positioning information for said instrument based on a relationship between said receiver assembly and said wireless transmitter.

2. The system of claim 1, wherein said positioning information comprises at least one of position and orientation of said instrument.

3. The system of claim 1, wherein said wireless transmitter comprises a wireless transmitter coil trio.

4. The system of claim 1, wherein said receiver assembly comprises two receiver coil trios.

5. The system of claim 1, wherein said relationship comprises triangulation between said wireless transmitter and said receiver assembly.

6. The system of claim 1, wherein said task involves manipulating said instrument outside of said user's line of sight.

7. The system of claim 1, wherein said instrument comprises a medical instrument.

8. The system of claim 1, further comprising a wired transmitter located away from said instrument.

9. The system of claim 7, wherein said wired transmitter is located on an instrument guide for said instrument.

10. The system of claim 1, wherein said receiver assembly is located on an instrument guide for said instrument.

11. The system of claim 1, wherein said positioning information is determined by a range and a gain ratio between said wireless transmitter and said receiver assembly.

12. The system of claim 1, wherein said positioning information is determining using mutual inductance between said wireless transmitter and said receiver assembly.

13. A method for tracking a position of an instrument, said method comprising:
    transmitting a signal from a wireless transmitter located on an instrument;
    receiving said signal at a receiver assembly; and
    determining positioning information for said wireless transmitter based on said signal and a relationship between said wireless transmitter and said receiver assembly.

14. The method of claim 13, further comprising transmitting a signal from a second transmitter to determine said position information.

15. The method of claim 13, wherein said determining step further comprises determining positioning information for said wireless transmitter by triangulating between said wireless transmitter and said receiver assembly.

16. The method of claim 13, wherein said determining step further comprises determining positioning information for said wireless transmitter by determining a range and a gain ratio between said wireless transmitter and said receiver assembly.

17. The method of claim 13, further comprising determining a magnitude and phase of said signal.

18. The method of claim 13, further comprising calculating a sum of products of said signal.

19. The method of claim 13, further comprising determining a mutual inductance between said wireless transmitter and said receiver assembly.

20. The method of claim 13, further comprising refining said positioning information using a solution fitter.

21. The method of claim 13, further comprising displaying said positioning information with respect to a reference system.

22. An improved wireless electromagnetic tracking system, said system comprising:
    a wireless transmitter coil trio attached to an object, said wireless coil trio transmitting a signal;
    a receiver assembly with at least two receiver coil trios; and
    a tracker electronics for determining positioning information for said wireless coil based on said wireless coil and said at least two receiver coil trios.

23. The system of claim 22, wherein said positioning information is determined based on said signal and a triangulation of signals between said wireless coil trio and said at least two receiver coil trios.

24. The system of claim 22, wherein said positioning information is determined based on a mutual inductance between said wireless coil trio and said at least two receiver coil trios.

25. The system of claim 22, wherein said position information is determined based on said signal and a gain ratio for said receiver assembly.

26. The system of claim 22, further comprising a display for displaying said positioning information.

* * * * *

UNITED STATES PATENT AND TRADEMARK OFFICE
CERTIFICATE OF CORRECTION

PATENT NO. : 7,015,859 B2  
APPLICATION NO. : 10/869396  
DATED : March 21, 2006  
INVENTOR(S) : Peter Traneus Anderson It is certified that error appears in the above-identified patent and that said Letters Patent is hereby corrected as shown below:

At col. 13, line 48, delete "$L_{mir}$" and insert --$L_{mtr}$--.

Signed and Sealed this

Eighth Day of August, 2006

JON W. DUDAS  
*Director of the United States Patent and Trademark Office*